United States Patent
Tichborne et al.

(10) Patent No.: US 9,354,099 B2
(45) Date of Patent: May 31, 2016

(54) AIRCRAFT FUEL LEVEL MEASUREMENT APPARATUS AND METHOD

(75) Inventors: Franklin Tichborne, Bristol (GB); James Beale, Bristol (GB)

(73) Assignee: AIRBUS OPERATIONS LIMITED, Bristol (GB)

( * ) Notice: Subject to any disclaimer, the term of this patent is extended or adjusted under 35 U.S.C. 154(b) by 1180 days.

(21) Appl. No.: 13/319,166

(22) PCT Filed: May 24, 2010

(86) PCT No.: PCT/GB2010/050845
§ 371 (c)(1),
(2), (4) Date: Nov. 7, 2011

(87) PCT Pub. No.: WO2010/139974
PCT Pub. Date: Dec. 9, 2010

(65) Prior Publication Data
US 2012/0065904 A1    Mar. 15, 2012

(30) Foreign Application Priority Data
Jun. 3, 2009 (GB) .................................. 0909510.0

(51) Int. Cl.
G01F 23/26 (2006.01)
G01F 19/00 (2006.01)

(52) U.S. Cl.
CPC ............ *G01F 23/266* (2013.01); *G01F 23/265* (2013.01)

(58) Field of Classification Search
CPC ... G01F 23/266; G01F 23/263; G01F 13/006; G01F 25/0061; B64D 37/00; G01R 27/2605

USPC .......................... 702/47, 50, 52, 55, 100, 104
See application file for complete search history.

(56) References Cited

U.S. PATENT DOCUMENTS

| 4,003,259 | A | * | 1/1977 | Hope ........................... 73/304 C |
| 4,099,167 | A | | 7/1978 | Pomerantz |
| 4,601,201 | A | | 7/1986 | Oota |
| 5,103,368 | A | * | 4/1992 | Hart ............................. 361/284 |
| 5,406,843 | A | | 4/1995 | Hannan |
| 6,318,172 | B1 | | 11/2001 | Byatt |
| 2010/0294035 | A1 | * | 11/2010 | Naydenov .................. 73/304 C |

FOREIGN PATENT DOCUMENTS

| DE | 19713267 A1 | 7/1998 |
| DE | 10008093 A1 | 9/2001 |
| EP | 1521065 A1 | 4/2005 |
| EP | 2034282 A1 | 3/2009 |

(Continued)

OTHER PUBLICATIONS

International Search Report for PCT/GB2010/050845 mailed Sep. 16, 2010.

(Continued)

*Primary Examiner* — Alexander Satanovsky
*Assistant Examiner* — Ivan Rabovianski
(74) *Attorney, Agent, or Firm* — Hauptman Ham, LLP

(57) ABSTRACT

A fuel level probe has a series of stacked, annular capacitors, the capacitance of which changes with the dielectric constant of the fluid in which they are immersed. A multiplexer provides sequential measurement of each capacitor to determine a step change in capacitance and hence fluid levels based on the time at which the capacitance changes.

10 Claims, 6 Drawing Sheets

(56) References Cited

FOREIGN PATENT DOCUMENTS

Figure 1:
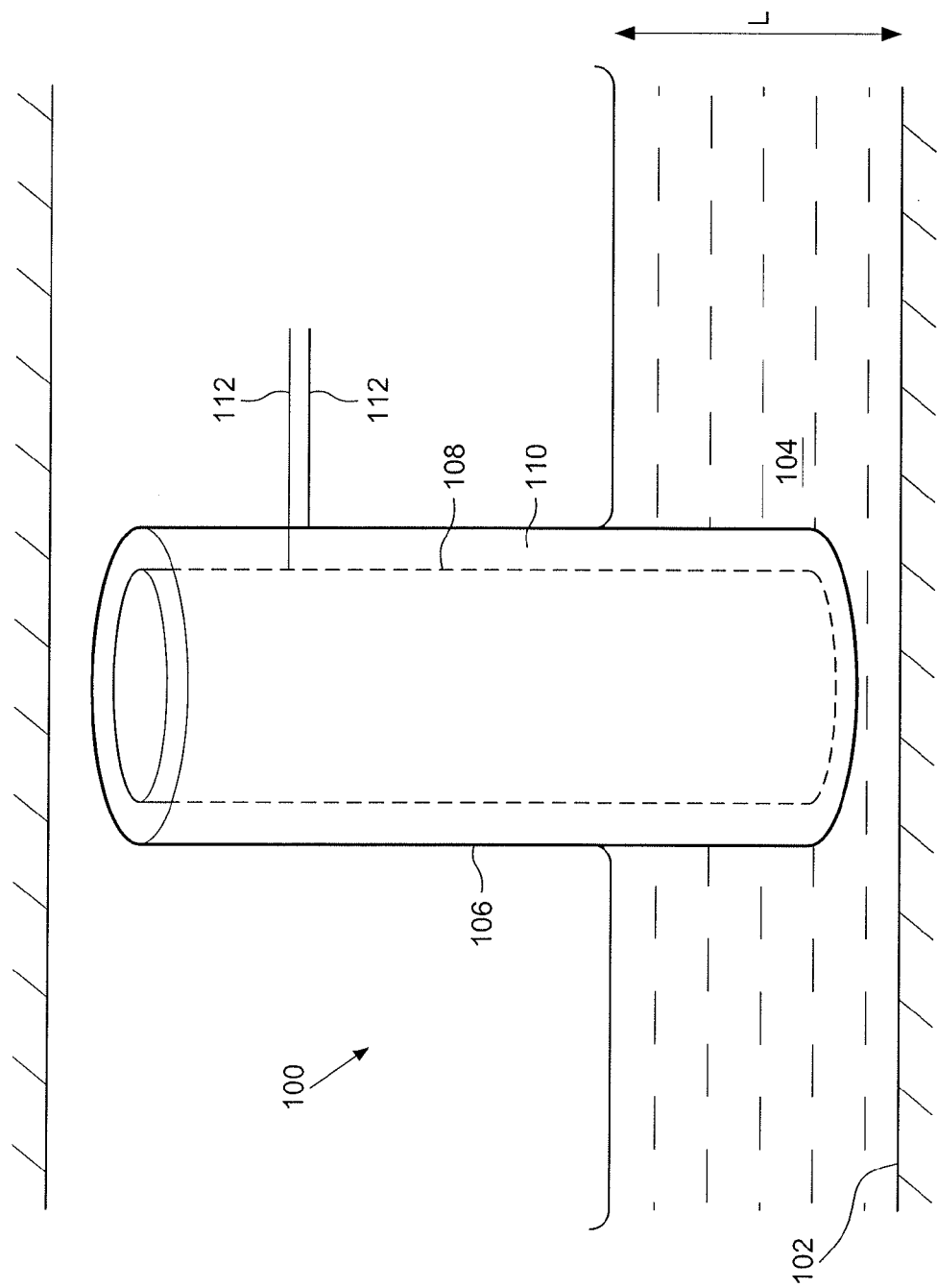

| JP | 60-192227 | A | 9/1985 |
| JP | 11-311562 | A | 11/1999 |
| WO | 96-33393 | A1 | 10/1996 |

OTHER PUBLICATIONS

International Preliminary Report on Patentability issued on Dec. 6, 2011.

* cited by examiner

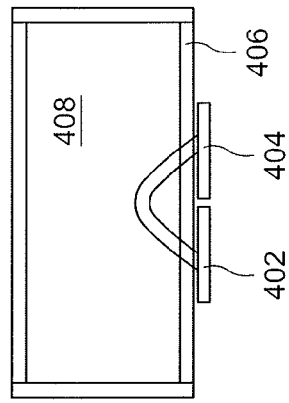
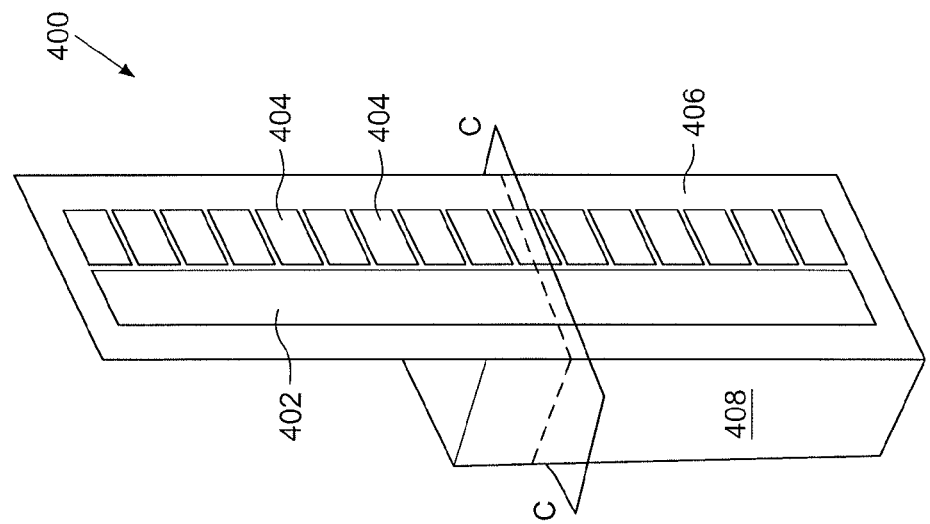
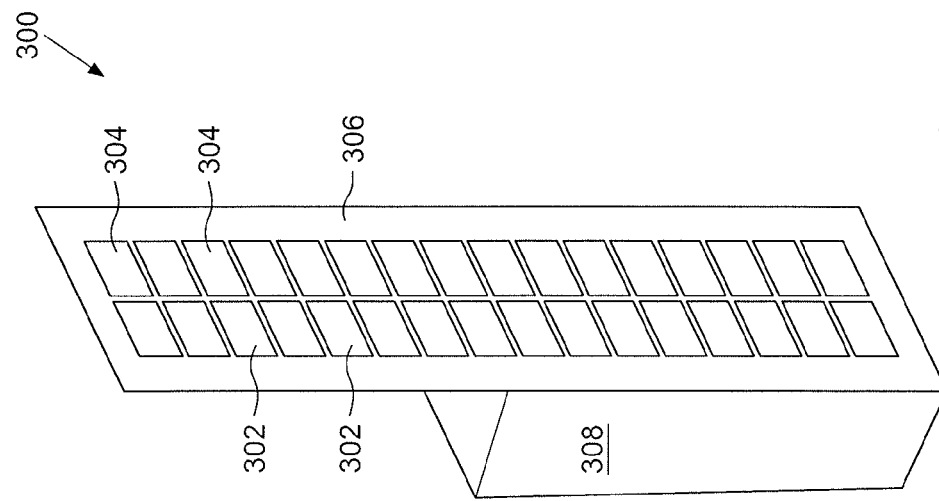

AIRCRAFT FUEL LEVEL MEASUREMENT APPARATUS AND METHOD

RELATED APPLICATIONS

The present application is a National Phase of International Application Number PCT/GB2010/050845, filed May 24, 2010 and claims priority from, British Application Number 0909510.0, filed Jun. 3, 2009.

The present invention is concerned with an aircraft fuel tank fluid level measurement apparatus and method for measurement of fluid levels in aircraft fuel tanks. More specifically, the present invention is concerned with an aircraft wing fuel tank fuel, water and ice level measurement apparatus and method.

Aircraft fuel tanks comprise vents in order to allow air in and out of the tank. This is because as the aircraft's altitude changes, the ambient pressure changes and therefore in order to avoid a significant pressure differential between the inside and outside of the fuel tank it is beneficial to allow ambient air to move in and out of the tank. This also allows air to replace the fuel used by the aircraft engines as the tank empties.

A problem with venting aircraft fuel tanks is that moist air may be allowed into the tank. When the moist air is cooled by a reduction in ambient temperature, the water in the air condenses to a liquid.

Fuel levels in modern aircraft are often monitored using a capacitive fuel probe. Such probes comprise a pair of offset plates (normally in the shape of a pair of concentric cylinders) between which fuel can enter. As the fuel level decreases, the annular area between the plates which contains fuel also decreases. Because the dielectric constant of the fuel is significantly higher than that of air, the capacitance of the probe changes with the fuel level, and can be measured in a low power circuit to determine the fuel level.

A problem with some such capacitive probes is that they operate on the assumption that the dielectric constant of the fuel is known and is constant, and therefore the capacitance of the probe is proportional to the fuel level. This may not be the case, as the dielectric constant may change with the pressure and temperature of the fuel.

One solution to this problem is that the dielectric constant of the fuel can be measured by using the fuel as the dielectric in a capacitor of known dimensions and properties. A problem with this approach is that the measurement equipment adds complexity and weight to the aircraft fuel system.

A further problem with known capacitive probes is that when the water level rises in the tank (as previously described) a stratified fluid develops in which the probe is partially immersed in water at its base, a layer of fuel on top of the water and the remainder in air. The reading of the probe is thus distorted because the dielectric constant of water (about 80 times that of air) is significantly higher than that of fuel. Therefore the probe will indicate a higher capacitance than the equivalent level of fuel alone and report that the tank contains more fuel than it actually does.

Capacitive probes have a large working range as they need to be able to report the fuel level from an empty to a full tank. A probe partially immersed in water will therefore not always provide a reading outside of its working range, rather it will report an erroneously high fuel level. Therefore the error is not always detectable by out-of-range readings. This is further complicated by the introduction of other substances such as ice.

Erroneous fuel readings are clearly undesirable. What is required is a fuel tank measurement system that can determine the level of each individual substance of a stratified substance an aircraft fuel tank.

It is an aim of the present invention to provide an improved fuel tank substance level detection apparatus and method.

According to a first aspect of the invention there is provided a method of detecting boundaries within a stratified substance in an aircraft fuel tank comprising the steps of: providing a capacitive fuel probe comprising a plurality of discrete capacitive sections, immersing the capacitive fuel probe in a stratified substance in an aircraft fuel tank, sequentially measuring the capacitance of each of the plurality of discrete capacitive sections at predetermined time intervals to create a time-domain output signal, detecting a change in the time-domain output signal, calculating the location of a boundary along the fuel probe within the stratified substance based on the time of the change in the time-domain output signal.

According to a second aspect of the invention there is provided a fuel level measurement apparatus comprising;

a capacitive fuel probe defining a fuel fill direction, the capacitive fuel probe having a plurality of discrete capacitive sections in the fuel fill direction, a circuit arranged to provide a time domain output signal representative of the capacitance of each of the plurality of discrete capacitive sections in turn, a processor configured to calculate the location of a boundary within a stratified substance in which the fuel probe is immersed from the time of a change in the time-domain output signal.

By providing an output signal in the time domain, the invention minimises wiring to the central fuel processing computer. Less wiring is advantageous in aircraft applications in order to minimise weight and interference. Further, by using the subject method, existing aircraft architecture may be used and the present invention retrofitted thereto.

All sections above the fuel level will have a first capacitance, and all below the fuel level will have a second, higher capacitance. Similarly, all sections below the water level (if present) will have a third capacitance higher than the second. In addition, if any ice has formed it will have a fourth capacitance higher than that of fuel, but lower than that of water. As such, by monitoring changes in the time domain signal as opposed to the absolute capacitance values, the dielectric constants of each constituent part of the stratified substance does not need to be known. This obviates the need for apparatus to measure or estimate the dielectric constants of the constituent substances.

Figure 2:
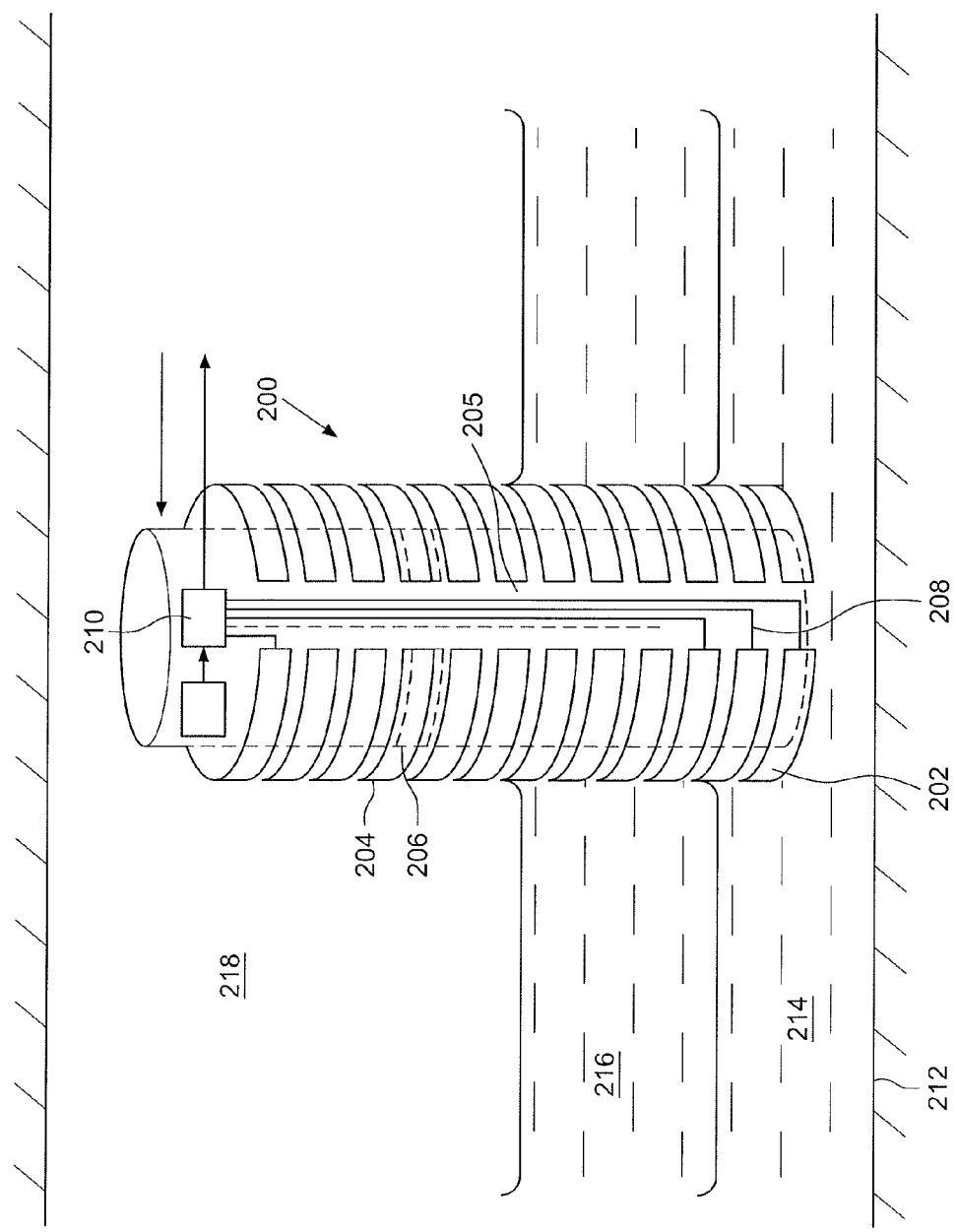
Figure 3:
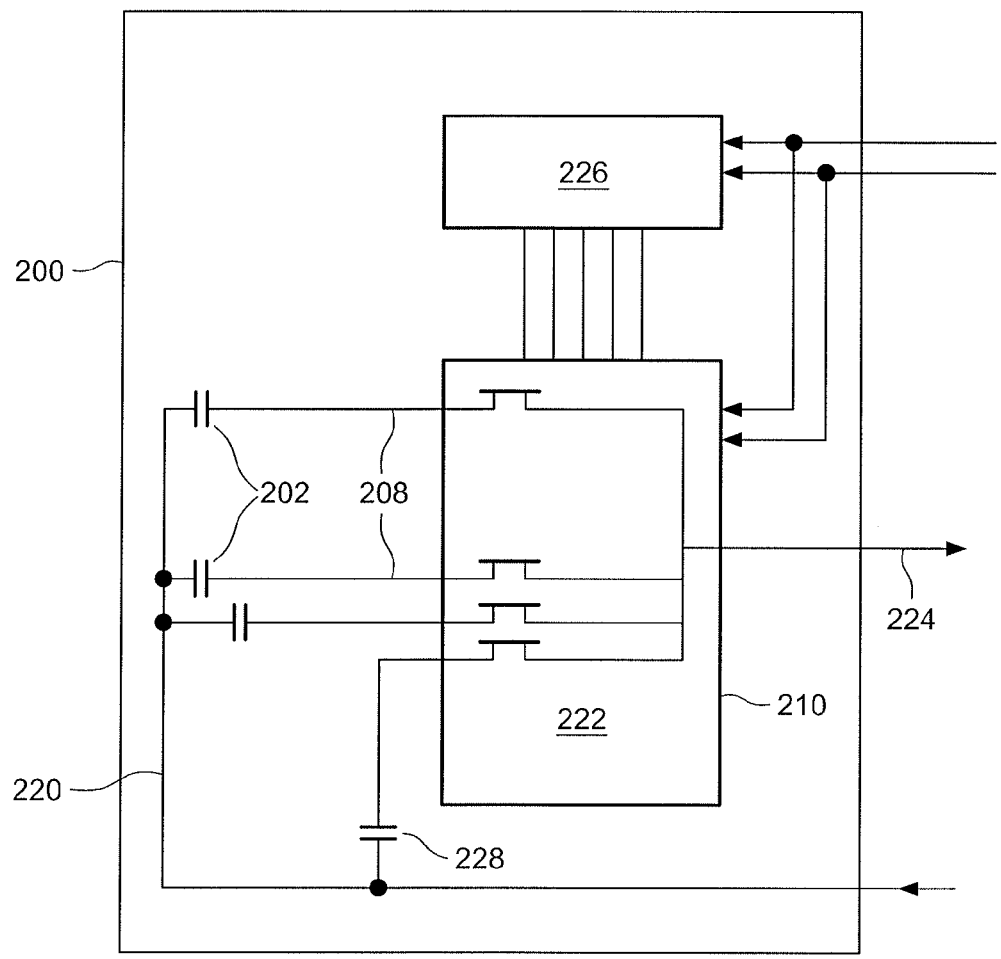
Figure 4:
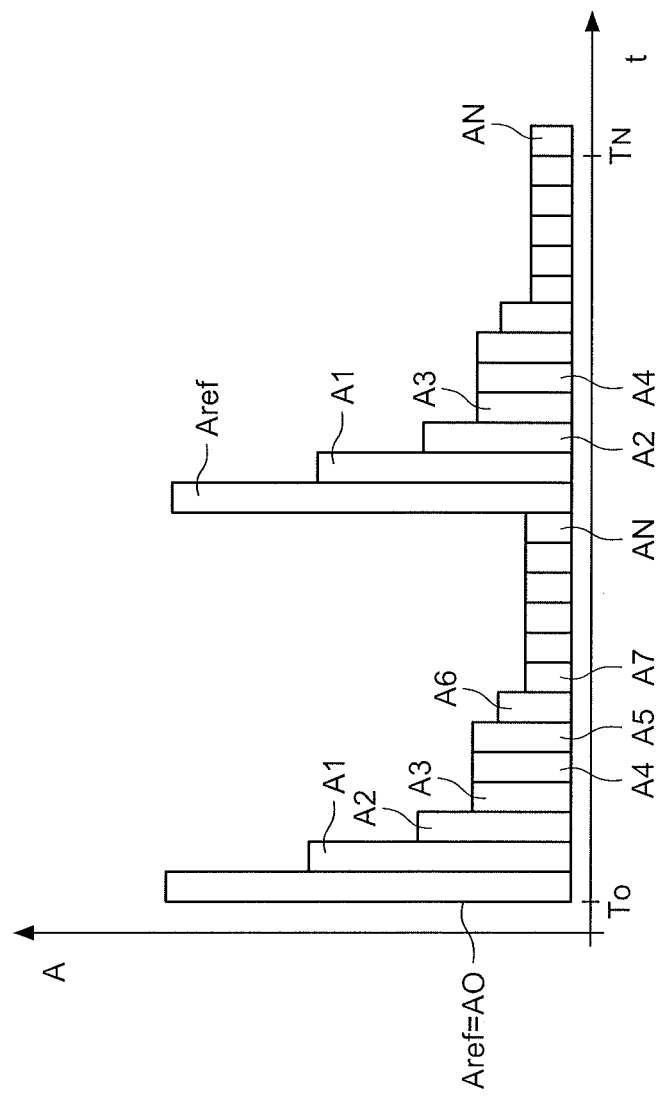
Figure 5:
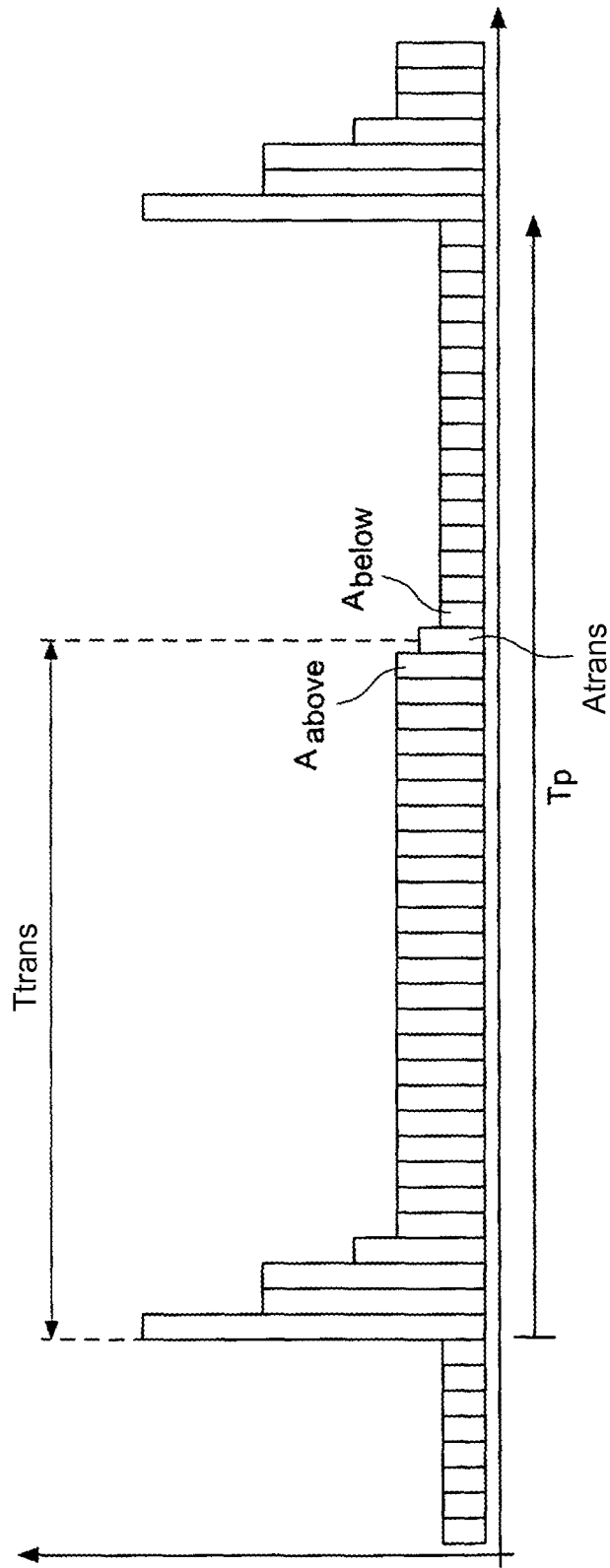

An example fuel level measurement apparatus and method in accordance with the present invention will not be described with reference to the accompanying figures in which:

FIG. 1 is a perspective view of a known capacitive probe,

FIG. 2 is a perspective view of a first capacitive probe in accordance with the present invention, FIG. 3 is a circuit diagram of the capacitive probe of FIG. 2, FIG. 4 is a graphic representation of the measured output of a probe according to the present invention, FIG. 5 is a further example of an output of a probe in accordance with the present invention, FIG. 6a is a perspective section view of a second capacitive probe in accordance with the present invention, FIG. 6b is a perspective section view of a third capacitive probe in accordance with the present invention, and, FIG. 6c is a section view of the capacitive probe of FIG. 6b.

Referring to FIG. 1, a capacitive probe 100 is installed within an aircraft wing fuel tank 102. The fuel tank 102 contains fuel 104 to a level L.

The capacitive probe 100 comprises an outer cylindrical plate 106 and an inner cylindrical plate 108 which are concentric. The cylindrical plates 106, 108 define an annular capacitor 110.

The probe 100 is not in contact with the tank 102 such that the fuel 104 can flow into, and out of, the capacitor 110. A pair of electrical contacts 112 are connected to the outer and inner plates 106, 108 for measurement of the capacitance of the probe 100 in a known fashion.

As the tank 102 fills and empties with the fuel 104, the capacitance of the probe 100 changes because the dielectric constant of air (filling the tank space) is significantly lower than that of fuel. Therefore, the level L of the fuel 104 in the tank can be estimated providing the dielectric constant of the fuel 104 is known.

As mentioned, a problem with this type of probe 100 is that the dielectric constant of fuel must be either estimated (introducing inaccuracies in the reading) or measured (which requires additional equipment).

Turning to FIG. 2, a probe 200 in accordance with the present invention is shown. The probe comprises a plurality of stacked annular sections 202, from 1 to "N" sections. Typically, N+1 is a power of 2 (e.g. 8, 16, 32, 64 etc.). Each section 202 comprises an outer plate 204 and a common inner plate 206 and each section 202 therefore acts independently as a capacitor. The outer plates 204 are etched onto the inner surface of a carrier (not shown). An axial gap 205 at a single circumferential position is formed in the outer plates 204. Each section 202 comprises its own set of contacts 208 etched into the carrier and routed through the gap 205 for use in measurement of its capacitance as will be described below. Each section 202 is identical, i.e. of equal height in the fuel fill direction, and equal diameter. Therefore each section can be assumed to have substantially the same capacitance properties when presented with the same dielectric substance.

Each of the contacts is connected to a multiplexing circuit 210 which will be described below.

As can be seen in FIG. 2, a fuel tank 212 in which the probe 200 is installed contains a layer of water 214 condensed from ingested atmospheric air (as described above). The tank also contains a layer of fuel 216 and the remainder is filled with air 218. The water 214 sinks to the bottom of the tank 212 because it is denser than the fuel 216.

As can be seen, the lowest of the annular sections 202 is completely immersed in water 214, the next of the annular sections 202 is partly immersed in water 214, and partly in fuel 216, the next three annular sections 202 are fully immersed in fuel 216, the next section is partly immersed in fuel 216 and partly immersed in the air 218, and the remaining sections 202 are exposed to the air 218 only.

This is typical of the situation in an aircraft wing fuel tank.

Referring to FIG. 3, the probe 200 is shown in circuit diagram form. Each of the N sections 202 is connected to one common contact 220, and the other to a 1:(N+1) analogue multiplexer 222 of the multiplexing circuit 210 via the contacts 208. The multiplexer 222 comprises an output 224 to a conventional capacitive probe measurement circuit (not shown) capable of measuring the capacitance between the common contact 220 and the output 224. An oscillator an m bit (where $2^m = N+1$) counter 226 is also provided to control the multiplexer 222.

A reference (sync) capacitor 228 is provided which is not affected by the contents of the fuel tank 212. The reference (sync) capacitor 228 is also connected to the common contact 220, the 1:(N+1) analogue multiplexer 222 (thus providing N+1 inputs). The capacitance of the reference capacitor 228, Aref, is significantly higher than the capacitance of any of the sections 202 when immersed in water, and is typically 1000 pF.

The multiplexer 222 is configured to switch sequentially from the reference capacitor 228 (at time T0) to each of the sections 202 in turn, starting from the lowermost section (at time T1) to the uppermost section (at time TN) and then returns to the reference capacitor 228 (at time T0) and repeats the sequence. The resulting series of measured capacitances (A) between the contacts 220 and 224 forms a time-domain output signal, shown in FIG. 4. Thus the output signal necessary to detect the fluid boundaries is contained entirely within the time domain.

Each capacitor returns a capacitance of An (n=0(ref), 1, 2, 3 . . . N) for a specific time interval "t" (a clocking period of the counter) determined by the oscillator and m bit counter 226. As can be see in FIG. 4, the reference capacitance Aref=A0 (at T0) is the highest. The capacitance A1 of the completely water immersed section is lower by design (as described above). The capacitance A2 of the next section is slightly lower still because it is partially immersed in fuel, which has a lower dielectric constant than water. The capacitances A3, A4, A5 of the next three capacitors are equal as they are all immersed in fuel. The capacitance A6 of the next section is slightly lower because it is only partially immersed in fuel, and the capacitance of the remaining sections A7 to AN is lower still because the dielectric constant of air is lower than that of fuel.

As can be seen, the cycle repeats starting with the reference capacitance Aref=A0 at T0.

The height of the probe 200 is known=Hp. The fuel and/or water level can be estimated by detecting a change in the capacitance at a specific time.

The complete cycle takes time Tp=(N+1)*t.

The time at which the capacitance changes from water to fuel (indicated by a drop in capacitance at A2) is denoted as Tw.

Therefore the water height can be calculated as Hw=Hp*(Tw/Tp).

The time at which the capacitance changes from water to fuel (indicated by a drop in capacitance at A6) is denoted as Tf.

Therefore the fuel height can be calculated as Hf=Hp*(Tf/Tp).

A more accurate method of determining the height of water and/or fuel can be used in which the capacitance of the transition probe (A2 or A6) is used.

Therefore a more accurate water height can be determined by:

$$Hwacc = Hp * \left[ \frac{Tw}{Tp} + \frac{A2 - A3}{N(A1 - A3))} \right]$$

A more accurate fuel height can be determined by:

$$Hfacc = Hp * \left[ \frac{Tf}{Tp} + \frac{A6 - A7}{N(A3 - A7))} \right]$$

Obviously, these methods are applicable generically, and following any change in capacitance, the height at which the dielectric constant changes (and hence fluid type changes) is calculated by:

$$H = Hp * \left[ \frac{Ttrans}{Tp} \right]$$

and accurately by:

$$Hacc = Hp * \left[ \frac{Ttrans}{Tp} + \frac{Atrans - Abelow}{N(Aabove - Abelow)} \right]$$

Where
Ttrans=the time at which the transition section provides the first change in capacitance,
Atrans=the capacitance of the transition section,
Abelow=the capacitance of the section preceding the transition section, and
Aabove=the capacitance of the section following the transition section,
as shown in FIG. 5.

The level H, which is not as accurate as Hacc, can be used for alarms (e.g. if water exceeds a predetermined height). The level Hacc can be used for more accurate readings of fuel or water quantity within the tank.

Many such readings are taken over a significant time interval (where Tp=1 second and 10 readings are taken over 10 seconds), which results are filtered to eliminate erroneous results from e.g. sloshing in the tank.

Because a time domain analogue capacitance (TDAC) probe as described above recognises changes in capacitance of the sections, the dielectric constants of the various fluids in the tank are not required. Therefore the invention offers significant advantages over known systems.

In the above embodiment, each section 202 where N+1=32, diameter of outer plate 204=20 mm, inner plate 206=16 mm, the capacitance:
in air=7.8 pF,
in fuel=16.5 pF (Jet-A)
in ice=32.5 pF
in water=625 pF.

Referring to FIG. 6a, an alternative a probe 300 in accordance with the present invention is shown. The probe 300 comprises a first plurality of stacked flat conductive sections 302, from 1 to "N" sections. Typically, N+1 is a power of 2 (e.g. 8, 16, 32, 64 etc.). Adjacent to (but not in contact with) the stacked flat sections 302 is a second plurality of stacked flat conductive sections 304. Thus, pairs of flat conductive sections are formed. The sections are mounted on the outer surface of an electrically insulating fuel tank wall 306 containing a fluid 308.

Each section 302, 304 is identical, i.e. of equal height in the fuel fill direction, and equal width. Therefore each pair of sections can be assumed to have substantially the same capacitance properties when presented with the same dielectric substance as will be described below.

Referring to FIG. 6b, a similar arrangement to that of FIG. 6a, but a probe 400 comprises a common flat conductive section 402 and a plurality of stacked flat conductive sections 404 proximate thereto. The sections 402, 404 are mounted on the outer surface of an electrically insulating fuel tank wall 406 containing a fluid 408.

Referring to FIG. 6c, a section through the plane C in FIG. 6b is shown. As can be seen, the electric field between the sections 402, 404 passes through the fluid 408 and as such the dielectric constant of the fluid will affect the capacitance between the common section 402 and each of the individual sections 404.

Variations of the above apparatus and method fall within the scope of the present invention.

The plates do not need to by cylindrical, and may be any shape as long as they define discrete capacitive regions.

A multiplexer does not have to be used; a less preferable option is to continuously and simultaneously read the capacitance of each section.

Instead of using multiple sets of outer plates, the probe may use a single, common outer plate and a plurality of inner plates. This may be advantageous if the capacitor is etched onto a carrier as it is easier to etch an outer surface of a carrier than an inner surface. Alternatively, sets of multiple opposed inner and outer plates may be used.

If N+1 is not a power of 2, the counter is modified to count from 0 to N+1 and repeat. The number of counter bits is then adjusted to the next highest power of 2.

The invention claimed is:

1. A method of detecting boundaries within a stratified substance in an aircraft fuel tank comprising:
   providing a capacitive fuel probe comprising a plurality of discrete capacitive sections,
   immersing the capacitive fuel probe in a stratified substance in an aircraft fuel tank,
   sequentially measuring a capacitance of each of the plurality of discrete capacitive sections at predetermined time intervals to create a time-domain output signal,
   providing a reference capacitor at a known position on the capacitive fuel probe, the reference capacitor having a capacitance outside of an expected capacitive range of each element of the stratified substance, and,
   detecting the reference capacitor by detecting the capacitance outside of the expected capacitive range of the stratified substance,
   detecting a change in the time-domain output signal,
   calculating a location of a boundary along the fuel probe within the stratified substance based on a time of the change in the time-domain output signal,
   in which the location of the boundary is calculated by determining the time between the detection of the reference capacitor and the detection of the change in the capacitance in the time-domain output signal.

2. The method of detecting boundaries according to claim 1 comprising:
   providing the reference capacitor at one end of the plurality of discrete capacitive sections.

3. The method of detecting boundaries according to claim 1 in which:
   the fuel probe comprises a multiplexer arranged to sequentially measure the capacitance of each of the discrete capacitive sections at the predetermined time intervals to create the time domain output signal.

4. The method of detecting boundaries according to claim 1 comprising the step of:
   calculating a precise location of the boundary within a discrete capacitive section by:
      determining a transition section having a transition capacitance,
      calculating the location of the boundary within the transition section by interpolating the transition capacitance with respect to the capacitance of the preceding discrete capacitive section and following discrete capacitive section in the time domain output signal.

5. A fuel level measurement apparatus comprising;
   a capacitive fuel probe defining a fuel fill direction, the capacitive fuel probe having a plurality of discrete capacitive sections in the fuel fill direction, a circuit arranged to provide a time domain output signal representative of the capacitance of each of the plurality of discrete capacitive sections in turn, a reference capacitor at a first position on an capacitive fuel probe, the reference capacitor having a capacitance outside of the expected capacitive range of each element of the stratified substance, a processor configured to calculate the location of a boundary within a stratified substance in which the fuel probe is immersed from a time of a change in the time-domain output signal, and, in which the processor is configured to calculate the location of the boundary by determining the time between the detection of the reference capacitor and the detection of the change in the time-domain output signal.

6. The fuel level measurement apparatus according to claim 5 in which the first reference capacitor is provided at one end of the plurality of discrete capacitive sections.

7. The fuel level measurement apparatus according to claim 5 comprising a multiplexer arranged to sequentially measure the capacitance of each of the discrete capacitive sections at a predetermined time interval to create the time domain output signal.

8. The fuel level measurement apparatus according to claim 7 in which the multiplexer is integral with the fuel probe.

9. The fuel level measurement apparatus according to claim 5 in which the processor is configured to:
 calculate a precise location of the boundary within a discrete capacitive section by:
  determining a transition section having a transition capacitance,
  calculating the location of the boundary within the transition section by interpolating the transition capacitance with respect to the capacitance of the preceding discrete capacitive section and following discrete capacitive section in the time domain output signal.

10. The fuel level measurement apparatus according to claim 5 in which each of the plurality of discrete capacitive sections is of equal length in the fuel fill direction.

\* \* \* \* \*